US007296893B2

(12) United States Patent
Dai

(10) Patent No.: US 7,296,893 B2
(45) Date of Patent: Nov. 20, 2007

(54) TRANSFORMATION METHODS OF WAVEFRONT MAPS FROM ONE VERTEX DISTANCE TO ANOTHER

(75) Inventor: Guangming Dai, Fremont, CA (US)

(73) Assignee: VISX, Incorporated, Santa Clara, CA (US)

( * ) Notice: Subject to any disclaimer, the term of this patent is extended or adjusted under 35 U.S.C. 154(b) by 394 days.

(21) Appl. No.: 11/032,469

(22) Filed: Jan. 7, 2005

(65) Prior Publication Data

US 2005/0195364 A1 Sep. 8, 2005

Related U.S. Application Data

(60) Provisional application No. 60/550,514, filed on Mar. 3, 2004.

(51) Int. Cl.
*A61B 3/10* (2006.01)
*A61B 3/00* (2006.01)
(52) U.S. Cl. ...................... 351/205; 351/246
(58) Field of Classification Search ............... 351/200, 351/204, 205, 211–216, 221, 246
See application file for complete search history.

(56) References Cited

U.S. PATENT DOCUMENTS

| 6,550,917 | B1 | 4/2003 | Neal et al. |
|---|---|---|---|
| 6,786,603 | B2 | 9/2004 | Altmann |
| 6,817,714 | B2 | 11/2004 | Altmann |
| 2003/0189690 | A1 | 10/2003 | Mihashi et al. |

OTHER PUBLICATIONS

Liang et al., "Objective measurement of wave aberrations of the human eye with the use of Hartmann-Shack wave-front sensor" *Journal of the Optical Society of America* (Jul. 1994) 11(7):1949-1957.

*Primary Examiner*—Scott J. Sugarman
(74) *Attorney, Agent, or Firm*—Townsend and Townsend and Crew LLP

(57) ABSTRACT

The present invention provides methods, systems and software for scaling optical aberration measurements of optical systems. In one embodiment, the present invention provides a method of reconstructing optical tissues of an eye. The method comprises transmitting an image through the optical tissues of the eye. Aberration data from the transmitted image is measured across the optical tissues of the eye at a first plane. A conversion algorithm is applied to the data, converting it to corrective optical power data that can be used as a basis for constructing a treatment for the eye at a second plane.

17 Claims, 9 Drawing Sheets

TRANSFORMATION METHODS OF WAVEFRONT MAPS FROM ONE VERTEX DISTANCE TO ANOTHER

CROSS-REFERENCE TO RELATED APPLICATIONS

This is a nonprovisional patent application which claims the benefit under 35 USC 119(e) of U.S. Provisional Patent Application No. 60/550,514 filed Mar. 3, 2004, the full disclosure of which is incorporated herein by reference.

BACKGROUND OF THE INVENTION

The present invention generally relates to scaling optical aberration measurements of optical systems. More particularly, the invention relates to improved methods and systems for processing optical power measurements taken at a first plane and converting those power measurements to corrective optical power measurements that can be used at a second plane. The present invention may be useful in any of a variety of ocular treatment modalities, including ablative laser eye surgery, contact lenses, spectacles, intraocular lenses, and the like.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, and the like.

Known corneal correction treatment methods have generally been successful in correcting standard vision errors, such as myopia, hyperopia, astigmatism, and the like. However, as with all successes, still further improvements would be desirable. Toward that end, wavefront measurement systems are now available to accurately measure the refractive characteristics of a particular patient's eye. One exemplary wavefront technology system is the VISX WaveScan® System, which uses a Hartmann-Shack wavefront lenslet array that can quantify aberrations throughout the entire optical system of the patient's eye, including first- and second-order sphero-cylindrical errors, coma, and third and fourth-order aberrations related to coma, astigmatism, and spherical aberrations.

Wavefront measurement of the eye may be used to create a high order aberration map or wavefront elevation map that permits assessment of aberrations throughout the optical pathway of the eye, e.g., both internal aberrations and aberrations on the corneal surface. The aberration map may then be used to compute a custom ablation pattern for allowing a surgical laser system to correct the complex aberrations in and on the patient's eye. Known methods for calculation of a customized ablation pattern using wavefront sensor data generally involves mathematically modeling an optical surface of the eye using expansion series techniques. More specifically, Zernike polynomials have been employed to model the optical surface, as proposed by Liang et al., in *Objective Measurement of Wave Aberrations of the Human Eye with the Use of a Harman-Shack Wave-front Sensor,* Journal Optical Society of America, July, 1994, vol. 11, No. 7, pp. 1949-1957, the entire contents of which is hereby incorporated by reference. Coefficients of the Zernike polynomials are derived through known fitting techniques, and the refractive correction procedure is then determined using the shape of the optical surface of the eye, as indicated by the mathematical series expansion model.

Optical measurements such as wavefront measurements are often taken at a measurement plane, whereas optical treatments may be needed at a treatment plane that is different from the measurement plane. Thus, power adjustments are often used when devising optical treatments for patients. For example, power adjustments can be used by optometrists when prescribing spectacles for patients. Typically, refractive measurements are made by an optometer at a measurement plane some distance anterior to the eye, and this distance may not coincide with the spectacle plane. Thus, the measured power corresponding to the measurement plane may need to be converted to a corrective power corresponding to the spectacle or treatment plane. Similarly, when wavefront measurements are obtained with wavefront devices, in many cases the measured map is conjugated at the pupil plane, which is not the same as the corneal plane or spectacle plane. To enhance the effectiveness of a refractive surgical procedure, vertex correction may be needed to adjust the power of the measured maps. Yet there remains a lack of efficient methods and systems for such power conversions.

Therefore, in light of above, it would be desirable to provide improved methods and systems for processing optical data taken at a measurement plane and converting that optical data to corrective optical data that can be used at a treatment plane.

BRIEF SUMMARY OF THE INVENTION

The present invention provides methods and systems for processing optical power measurements taken at a first plane and converting those power measurements to corrective optical power measurements that can be used at a second plane.

In one aspect, the present invention provides a method of determining a refractive treatment shape for ameliorating a vision condition in a patient. The method comprises measuring a wavefront aberration of an eye of the patient in order to provide a measurement surface aberration, deriving a treatment surface aberration of the eye based on the measurement surface aberration, and determining the refractive treatment shape based on the treatment surface aberration of the eye. The wavefront aberration can correspond to a measurement surface that is disposed at or near a pupil plane of the eye, and the treatment surface aberration can correspond to a treatment surface that is disposed at or near an anterior surface of a cornea of the eye. The treatment surface aberration may be derived using a difference between the measurement surface and the treatment surface.

In another aspect, the present invention provides a method of ameliorating a vision condition in a patient. The method comprises measuring a wavefront aberration of an eye of the patient in order to provide a measurement surface aberration, deriving a treatment surface aberration of the eye from the measurement surface aberration, determining a refractive treatment shape based on the treatment surface aberration of the eye, and applying the refractive treatment shape to the eye of the patient to ameliorate the vision condition. The wavefront aberration can correspond to a measurement surface that is disposed at or near a pupil plane of the eye. The treatment surface aberration can correspond to a treatment surface that is disposed at or near an anterior corneal surface of the eye, or a treatment surface that corresponds to a spectacle plane of the eye. Relatedly, the treatment surface may be disposed posterior to a pupil plane of the eye. The treatment surface aberration may be based on a difference between the measurement surface and the treatment surface.

In a related aspect, the refractive treatment shape can be applied to the eye of the patient in a variety of treatment modalities. For example, the treatment shape can be applied by ablating a corneal surface of the patient to provide a corneal surface shape that corresponds to the refractive treatment shape. The treatment shape may also be applied by providing the patient with a contact lens that has a shape that corresponds to the refractive treatment shape. Further, the treatment shape may be applied by providing the patient with a spectacle lens that has a shape that corresponds to the refractive treatment shape. What is more, the treatment shape can be applied by providing the patient with an intra-ocular lens that has a shape that corresponds to the refractive treatment shape.

In another aspect, the present invention provides a system for generating a refractive treatment shape for ameliorating a vision condition in an eye of a patient. The system comprises an input module that accepts a measurement surface aberration, a transformation module that derives a treatment surface aberration based on the measurement surface aberration, and an output module that generates the refractive treatment shape based on the treatment surface aberration. The measurement surface aberration may be based on a wavefront aberration of the eye. The wavefront aberration can correspond to a measurement surface that is disposed at or near a pupil plane of the eye. The treatment surface aberration can correspond to a treatment surface that is disposed at or near an anterior corneal surface of the eye, or a treatment surface that corresponds to a spectacle plane of the eye. Relatedly, the treatment surface may be disposed posterior to a pupil plane of the eye. The treatment surface aberration may be based on a difference between the measurement surface and the treatment surface.

In another aspect, the present invention provides a system for ameliorating a vision condition in an eye of a patient. The system comprises an input module that accepts a measurement surface aberration, a transformation module that derives a treatment surface aberration based on the measurement surface aberration, an output module that generates a refractive treatment shape based on the treatment surface aberration, and a laser system that directs laser energy onto the eye according to the refractive treatment shape so as to reprofile a surface of the eye from an initial shape to a subsequent shape, the subsequent shape having correctively improved optical properties for ameliorating the vision condition. The measurement surface aberration may be based on a wavefront aberration of the eye. The wavefront aberration can correspond to a measurement surface that is disposed at or near a pupil plane of the eye, and the treatment surface aberration can correspond to a treatment surface that is disposed at or near an anterior surface of a cornea of the eye. The treatment surface aberration can be derived based on a difference between the measurement surface and the treatment surface.

In some aspects, the treatment surface aberration may be a treatment surface wavefront map. In other aspects, the measurement surface aberration may be a measurement surface wavefront map. The treatment surface wavefront map may be derived at least in part by local slope scaling of the measurement surface wavefront map. In still other aspects, the treatment surface wavefront map may be derived at least in part by applying a scaling factor of $1/(1+Pd)$ to a slope of the measurement surface wavefront map, where P represents a local curvature of the measurement surface wavefront map and d represents a difference between the measurement surface and the treatment surface. In a related aspect, a difference between the measurement surface and a retinal surface of the eye corresponds to a first vertex measure, and a difference between the treatment surface and the retinal surface of the eye corresponds to a second vertex measure. P may be based on a second derivative of the measurement surface wavefront map. P may also be based on a pupil radius of the eye.

In some aspects, the treatment surface wavefront map can be derived according to an iterative Fourier reconstruction algorithm. What is more, the measurement surface aberration may reflect low order and/or high order aberrations of the eye of the patient.

In another aspect, the present invention provides a system for generating a prescription for ameliorating a vision condition in an eye of a patient. The system comprises an input that accepts irregular aberration data corresponding to an aberration measurement surface adjacent a pupil plane of the eye, a transformation module that derives a treatment surface aberration corresponding to a treatment surface that is disposed adjacent an anterior surface of a cornea of the eye, and an output module that generates the prescription based on the treatment surface aberration. The treatment surface aberration can be derived from the irregular aberration data using a difference between the measurement surface and the treatment surface.

These and other aspects will be apparent in the remainder of the figures, description, and claims.

DETAILED DESCRIPTION OF THE INVENTION

The present invention provides methods, software, and systems for processing optical power measurements taken at a first plane and converting those power measurements to corrective optical power measurements that can be used at a second plane.

The present invention is generally useful for enhancing the accuracy and efficacy of laser eye surgical procedures, such as photorefractive keratectomy (PRK), phototherapeutic keratectomy (PTK), laser in situ keratomileusis (LASIK), and the like. The present invention can provide enhanced optical accuracy of refractive procedures by improving the methodology for processing measured optical errors of the eye and hence calculate a more accurate refractive ablation program. In one particular embodiment, the present invention is related to therapeutic wavefront-based ablations of pathological eyes.

The present invention can be readily adapted for use with existing laser systems, wavefront measurement systems, and other optical measurement devices. While the systems, software, and methods of the present invention are described primarily in the context of a laser eye surgery system, it should be understood the present invention may be adapted for use in alternative eye treatment procedures and systems such as spectacle lenses, intraocular lenses, contact lenses, corneal ring implants, collagenous corneal tissue thermal remodeling, and the like.

Figure 1:
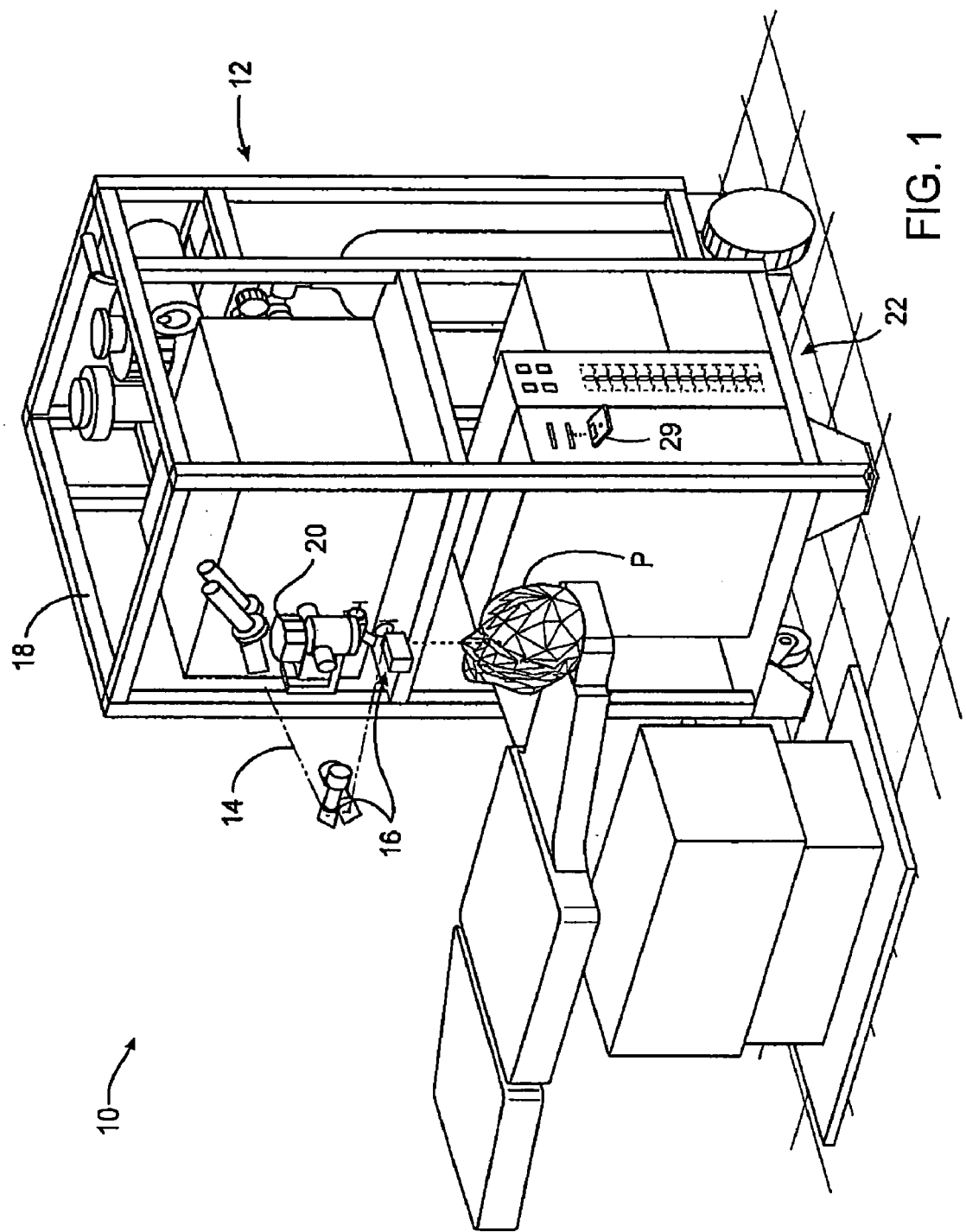
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 215 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modem computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315, 413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Basis data can be further characterized for particular lasers or operating conditions, by taking into account localized environmental variables such as temperature, humidity, airflow, and aspiration.

Figure 2:
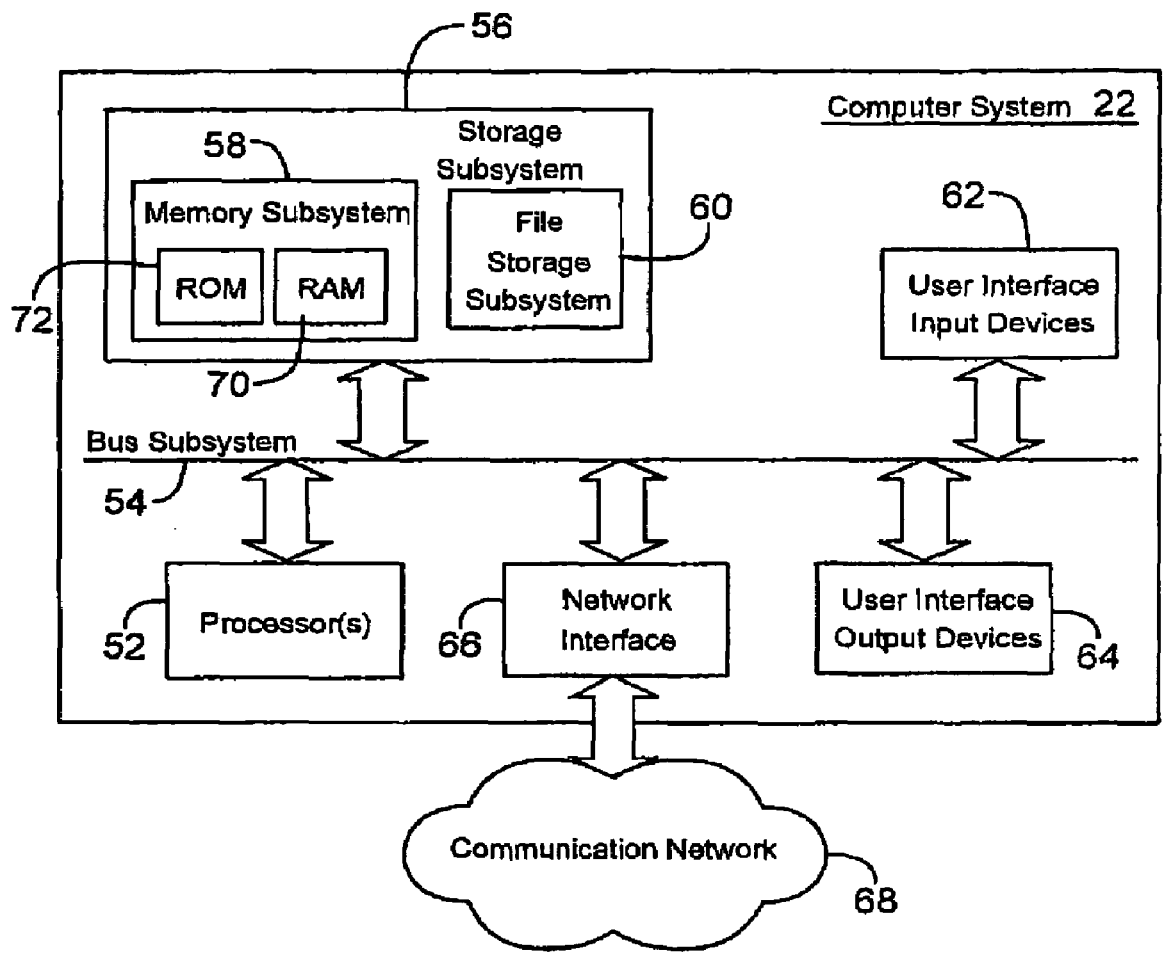
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
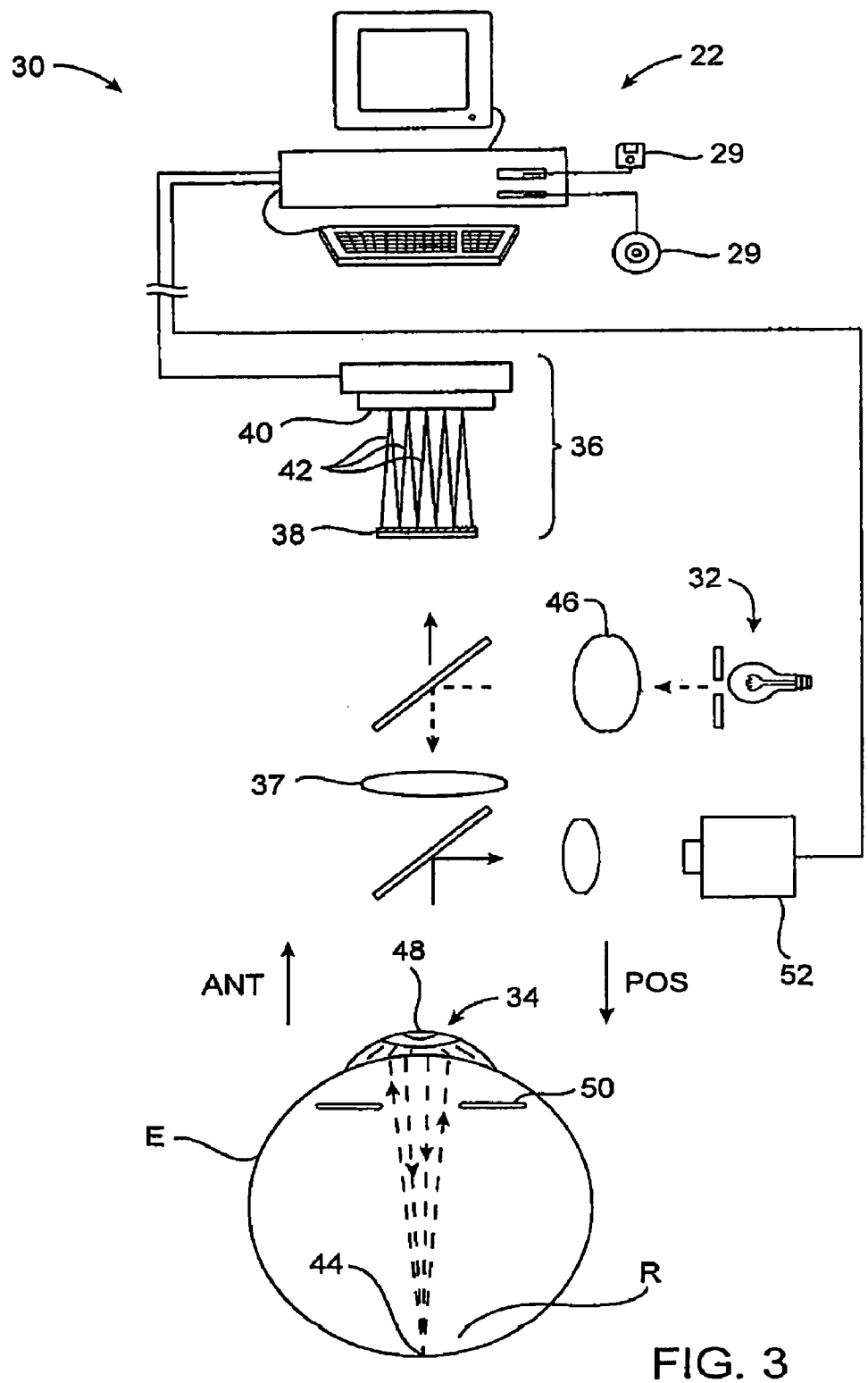
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
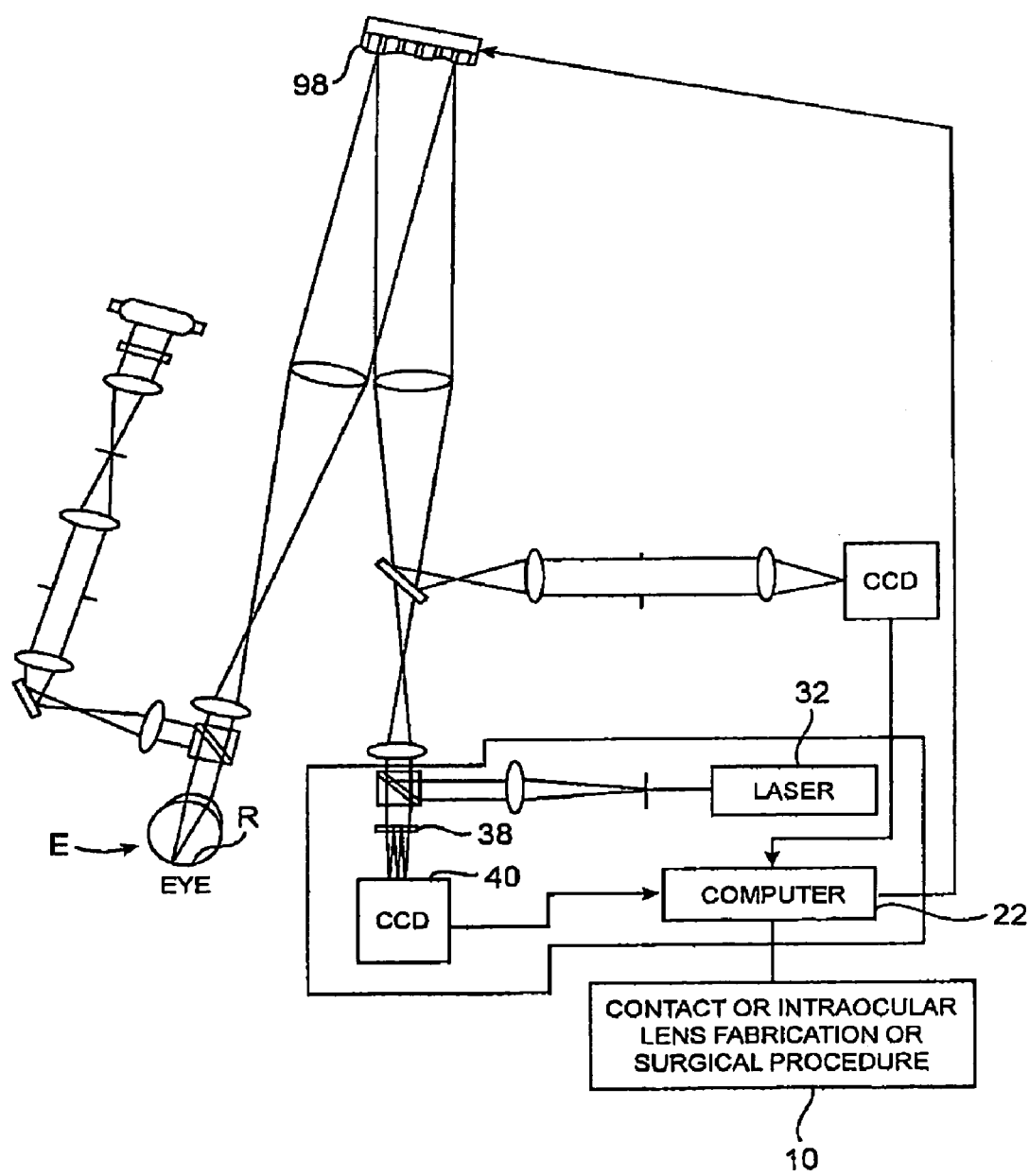
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations comprise elements of a VISX WaveScan®, available from VISX, INCORPORATED of Santa Clara, Calif. One embodiment includes a WaveScan® with a deformable mirror as described above. An alternate embodiment of a wavefront measuring system is described in U.S. Pat. No. 6,271,915, the full disclosure of which is incorporated herein by reference.

Figure 4:
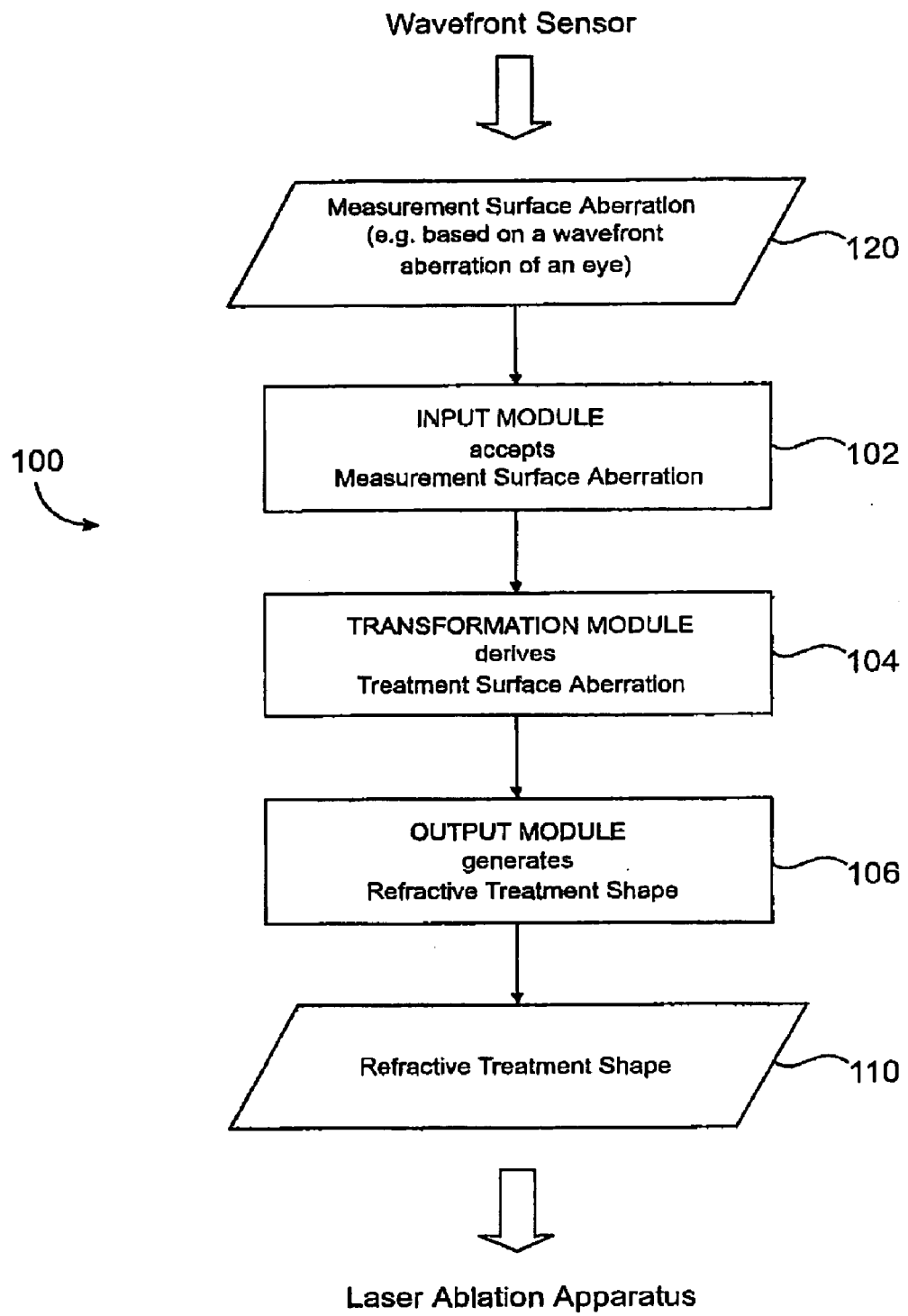
FIG. 4 schematically represents a simplified set of modules that carry out one method of the present invention.

FIG. 4 schematically illustrates a simplified set of modules, or a correction system 100, for carrying out a method according to one embodiment of the present invention. Correction system 100 can be integrated or interfaced with, for example, computer system 22, or otherwise used in conjunction with laser surgical system 10. The modules may be software modules on a computer readable medium that is processed by processor 52 (FIG. 2), hardware modules, or a combination thereof. Any of a variety of commonly used platforms, such as Windows, MacIntosh, and Unix, along with any of a variety of commonly used programming languages, may be used to implement the present invention.

Correction system 100 can be configured to generate a refractive treatment shape 110 for ameliorating a vision condition in a patient. An input module 102 typically receives a measurement surface aberration 120, such as wavefront aberration data from wavefront sensors, which characterize aberrations and other optical characteristics of the entire optical tissue system imaged. Often, the wavefront aberration corresponds to a measurement surface that is disposed at or near a pupil plane of the eye. The data from the wavefront sensors are typically generated by transmitting an image (such as a small spot or point of light) through the optical tissues, as described above. Measurement surface aberration 120 can include an array of optical gradients or a gradient map.

Correction system 100 can include a transformation module 104 that derives a treatment surface aberration. The treatment surface aberration can correspond to a treatment surface that is disposed at or near an anterior corneal surface of the eye, or a treatment surface that corresponds to a spectacle plane of the eye. Relatedly, the treatment surface may be disposed posterior to a pupil plane of the eye. Often, the treatment surface aberration is derived from measurement surface aberration 120 using a difference between the measurement surface and the treatment surface. For example, optical gradient data from input module 102 may be transmitted to transformation module 104, where a treatment surface aberration is mathematically reconstructed based on the optical gradient data.

Correction system 100 can include an output module 106, such that the treatment surface aberration generated by transformation module 104 can then be transmitted to output module 106 where a refractive treatment shape 110 can be generated based on the treatment surface aberration. Refractive treatment shape 110 may be transmitted to a laser treatment apparatus for generation of a laser ablation treatment for the patient. Similarly, refractive treatment shape 110 may form the basis for fabrication of contact lenses, spectacles, or intra-ocular lenses.

As can be appreciated, the present invention should not be limited to the order of steps, or the specific steps illustrated, and various modifications to the method, such as having more or less steps, may be made without departing from the scope of the present invention.

Figure 5:
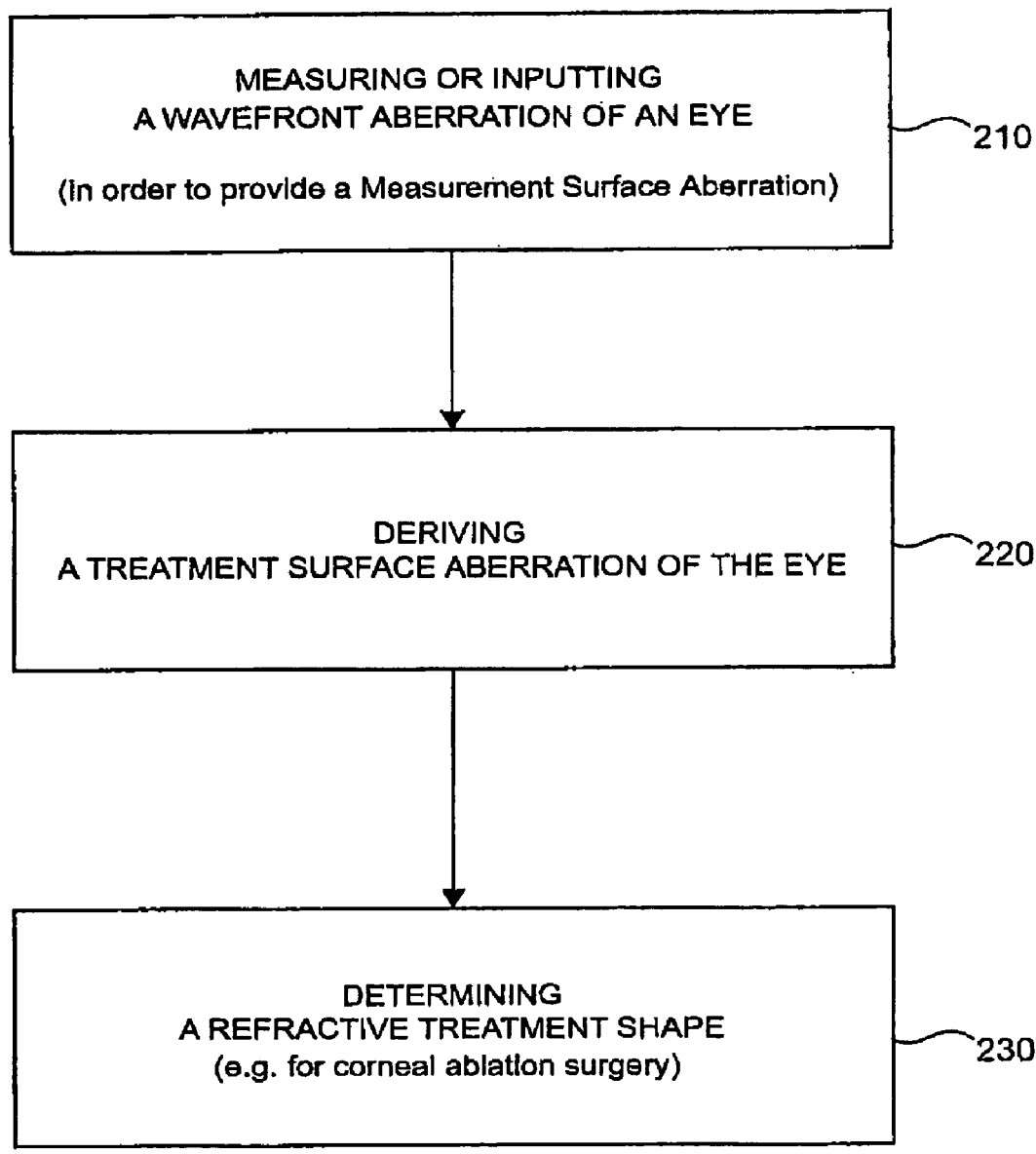
FIG. 5 is a flow chart that schematically illustrates a method of determining a refractive treatment shape according to one embodiment of the present invention.

In one embodiment, the present invention provides a method of determining a refractive treatment shape for ameliorating a vision condition in a patient. FIG. 5 depicts the steps of an exemplary method according to the present invention. The refractive treatment shape can be based on a treatment surface aberration that is derived from a measurement surface aberration.

I. Measurement Surface Aberration

In general terms, a measurement surface aberration can be determined from optical data corresponding to a measurement surface. For example, a measurement surface aberration can be determined by measuring a wavefront aberration of an eye of a patient. A wavefront measurement system that includes a wavefront sensor (such as a Hartmann-Shack sensor) may be used to obtain one or more measurement surface aberrations (e.g. wavefront maps) of the optical tissues of the eye. The wavefront map may be obtained by transmitting an image through the optical tissues of the eye and sensing the exiting wavefront surface. From the wavefront map, it is possible to calculate a surface gradient or gradient map across the optical tissues of the eye. A gradient map may comprise an array of the localized gradients as calculated from each location for each lenslet of the Hartmann-Shack sensor.

A. Measurement Surface

There are a variety of devices and methods for measuring surface characteristics of optical systems. The category of aberroscopes or aberrometers includes classical phoropter and wavefront approaches. Classical phoropters can be used to record optical data corresponding to a measurement surface that is disposed anterior to the cornea of an eye. For example, phoropters can measure low order aberrations at a distance of about 12.5 mm anterior to the corneal surface. In many cases, this will correspond to a spectacle plane of the eye. Wavefront devices are often used to measure both low order and high order aberrations adjacent a pupil plane, which can be about 3.5 mm posterior to the corneal surface. Another category of measuring approaches includes topography based measuring devices and methods. Topography typically involves providing optical data corresponding to a measurement surface that is disposed at or near the corneal surface of the eye.

B. Aberration

As noted above, the measurement surface aberration can be based on a refractive measurement as determined by an optometer, or any of a wide variety of devices for obtaining irregular aberration data. Similarly, the measurement surface aberration can be a measurement surface wavefront map, as determined by a wavefront measurement device. What is more, the measurement surface aberration may reflect both low order and high order aberrations of the eye of a patient.

II. Treatment Surface Aberration

When a measurement surface aberration of an optical system has been determined, it is then possible to derive a treatment surface aberration of the optical system. In the case of refractive surgical methods, for example, a treatment surface aberration corresponding to a corneal plane can be derived from a measurement surface aberration as determined in a plane other than the corneal plane.

A. Treatment Surface

The treatment surface aberration corresponds to a treatment surface, which is typically disposed at or near an anterior surface of a cornea of an eye. Often, the treatment surface will correspond to a corneal plane associated with the eye, as in the case of ablative laser eye surgery or contact lens treatments. At other times, the treatment surface may correspond to a spectacle plane associated with the eye, as in the case of spectacle treatments. Further, the treatment surface can be posterior to the pupil plane of the eye, as in the case of intraocular lens treatments.

B. Derivation of Treatment Surface Aberration

The treatment surface aberration can be derived from the measurement surface aberration, based on a difference between the measurement surface and the treatment surface. The difference between the measurement surface and the treatment surface, for example, can include a distance measurement that represents a difference between the two surfaces. In some embodiments, the distance measurement is based on a vertex distance difference, the vertex distance difference reflecting a distance between a vertex of the measurement surface and a vertex of the treatment surface.

1. Classical Vertex Correction Formulas

Figure 6:
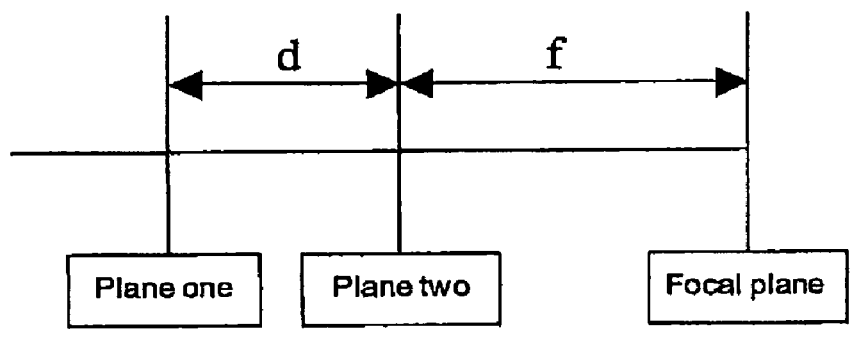
FIG. 6 illustrates a model optical system.

Traditionally, the power of a lens is measured in diopters, and can be defined as the reciprocal of the lens focal length in meters. FIG. 6 shows a schematic diagram of an optical system. The system includes a first plane disposed at a first distance from a focal plane, the first distance corresponding to a first focal length, and a second plane disposed at a second distance from the focal plane, the second distance corresponding to a second focal length. Although the first and second planes are illustrated as flat surfaces, these planes can also represent curved surfaces such as lenses, wavefronts, and other representations of optical surfaces. In the exemplary optical system depicted by FIG. 6 legend (a), the focal plane may be associated with a retinal plane, the first plane may be associated with a spectacle plane, and the second plane may be associated with a corneal plane.

A treatment surface can correspond to, or be based upon, a spectacle surface, corneal surface, pupil surface, and the like. A spectacle surface is typically about 12.5 mm anterior to the cornea of the eye. A pupil surface or plane is typically about 3.5 mm posterior to the cornea of the eye. An intraocular lens surface is usually about 0.5 mm posterior to the pupil surface or plane of the eye. A contact lens surface is typically at or slightly anterior to the cornea of the eye. If the treatment surface and the measurement surface are substantially in the same plane, there may be no need for a vertex correction.

When prescribing spectacles, for example, an optometrist may first make or consider an aberration measurement such as a refractive measurement of the eye, where the aberration measurement corresponds to a measurement surface at or near a pupil plane or surface of the eye. Because the treatment surface may not be the same as the measurement surface, it is often desirable to make a power adjustment in order to determine the corrective surface shape or treatment surface aberration. In the case of spectacles, the treatment surface is disposed anterior to the corneal surface, usually by about 12.5 mm.

Likewise, when prescribing contact lenses, an optometrist can consider a refractive correction corresponding to the spectacle plane, and make a power adjustment to account for the difference between the spectacle plane and the corneal plane. In this case, the adjustment often depends on a vertex distance, corresponding to the distance between the posterior surface of the spectacle lens and the anterior surface of the cornea.

Thus, given a measurement surface aberration, it is possible to derive a treatment surface aberration based on a difference between the treatment surface and the measurement surface. Often, the difference will be a vertex distance between the treatment surface and the measurement surface. As further discussed below, the treatment surface aberration can then be used to determine a refractive treatment shape. In the case of corrective spectacles, the refractive treatment shape can be a basis for a prescription for the patient, where the treatment shape corresponds to the spectacle plane or surface.

Typically, the measurement surface aberration corresponds to a first power data, and the treatment surface aberration corresponds to a derived second power data. The second power data can be derived from the first power data and the distance between the measurement surface and the treatment. To achieve the effect of a power change, in terms of a vertex correction, a vertex distance measure can be based on a difference between the measurement surface and the treatment surface. The vertex correction represents a power change between the first power data and the second power data. In this sense, the derivation of the second power corresponds to a vertex correction of the first power. The vertex of a lens curve can be defined as the apex of the lens curve, or as the point on the lens curve in which the lens curve axis intersects it.

a. Traditional (Non Wavefront)

Traditional phoropters can be used to make traditional optical aberration measurements such as sphere and cylinder. Such aberration measurements are often expressed in terms of dioptric power. Referring again to FIG. 6 legend (a), assuming the power corresponding to the second plane, e.g. a corneal plane, is S, and the power corresponding the first plane, e.g. a spectacle plane, is S', it is possible to describe the relationship between the two powers with the following equations.

$$S = \frac{1}{f}, \tag{1}$$

$$S' = \frac{1}{f+d} \tag{2}$$

$$= \frac{S}{1+dS}$$

Power can be expressed in units of diopters. f represents the distance between the focal plane and the second plane, although here this term is not a factor in the relationship between the two power measurements S and S'. d represents the vertex distance between the first and second planes. Where a first plane treatment surface is disposed anterior to a second plane measurement surface, d will typically have a positive value. For example, for spectacle treatments, d can be about 0.0125 m, and for refractive surgery treatments, d can be about 0.0035 m. Conversely, where the first plane treatment shape is disposed posterior to a second plane measurement surface, d will typically have a negative value. For example, for intraocular lens treatments, d can be about −0.0005 m.

Sphere is a low order aberration corresponding to defocus, and cylinder is a low order aberration corresponding to astigmatism. To consider a combination of sphere and cylinder powers, it is possible to replace S by (S+C) where C stands for cylinder power at the maximum meridian. Thus, cylinder at the spectacle plane can be represented by C', where $$C' = \frac{S+C}{1+d(S+C)} - S'. \tag{3}$$

These formulae can be used to calculate the power change associated with a vertex distance.

b. Wavefront

In addition to the traditional phoropter approaches discussed above, it is also possible to evaluate optical systems based on wavefront analysis. Wavefront analysis can be useful in evaluating low order and high order aberrations. Referring again to FIG. 6, it is possible to consider the first and second planes as associated with a general wavefront. The wavefront can begin at a virtual focal point corresponding to the focal plane, and propagate from plane two toward plane one. For each point along the wavefront surface, a local slope can be calculated. For example, the local slope can be the first derivative of the surface at a certain point. The local slope reflects a surface value at that point, as well as the surface values of the surrounding points. The local slope can be a direction-dependent vector. Because the wavefront local slopes are proportional to the local focal length, as the wavefront is propagated forward, the slope of the wavefront can be scaled by a factor of a such that:

$$\alpha = \frac{f}{f+d} \quad (4)$$

where f is the focal length of the wavefront and d is the vertex distance. Here, the vertex distance can represent a difference between the measurement surface, or plane two, and the treatment surface, or plane one. Thus, by making an initial measurement of the wavefront at plane two, it is possible to calculate a new wavefront surface at plane where individual points on the new surface have a local curvature that is derived by the scaling factor as discussed above. In the exemplary optical system depicted by FIG. 6 legend (b), the first plane can represent a corneal plane, the second plane can represent a pupil plane, and the focal plane can represent a retinal plane. If the treatment surface is anterior to the measurement surface, then the vertex distance is positive, and if the treatment surface is posterior to the measurement surface, then the vertex distance is negative. Similarly, for the myopia case, because the power is negative, the focal length could take a negative value. Generally a can have a positive value, as the absolute value of f is often much larger than d.

As discussed above, vertex correction can be used with traditional aberrometry approaches. It is also possible to use vertex correction with wavefront approaches. Here, W(x,y) represents the wavefront at the measurement plane and W'(x,y) represents the wavefront at the treatment plane with vertex distance of d. The local slope is assumed to be scaled, as discussed above. Thus, the following equations are partial derivatives of the corrected wavefront at the treatment plane.

$$\frac{\partial W'}{\partial x} = \frac{f}{f+d} \frac{\partial W}{\partial x} \quad (5)$$

$$\frac{\partial W'}{\partial y} = \frac{f}{f+d} \frac{\partial W}{\partial y}$$

It can be demonstrated that the classical formula for vertex correction holds with the assumption that the local slopes can be scaled according to a scaling factor of f/(f+d). The following examples illustrate this principle with respect to (i) sphere, or defocus, (ii) cylinder, or astigmatism, (iii) coma, and (iv) spherical aberration. Wavefronts can be expressed in terms of polynomial equations. This equation is useful for the derivations that follow.

$$\frac{\partial^2 W'}{\partial r^2} = \frac{x^2}{x^2+y^2} \frac{\partial^2 W'}{\partial x^2} + \frac{2xy}{x^2+y^2} \frac{\partial^2 W'}{\partial x \partial y} + \frac{y^2}{x^2+y^2} \frac{\partial^2 W'}{\partial y^2}. \quad (6)$$

(i) Sphere

In the following discussion, Zernike polynomials are used to represent the ocular aberrations. Starting with a sphere, where $W(r)=c_2^0\sqrt{3}(2r^2-1)$, corresponding to the wavefront at the second plane, the curvature of the converted wavefront W'(r) at the first plane can be expressed as $$\frac{\partial^2 W'}{\partial r^2} = \frac{x^2}{x^2+y^2} \frac{\partial^2 W'}{\partial x^2} + \frac{2xy}{x^2+y^2} \frac{\partial^2 W'}{\partial x \partial y} + \frac{y^2}{x^2+y^2} \frac{\partial^2 W'}{\partial y^2} \quad (7)$$

$$= 4\sqrt{3}\, c_2^0 \frac{f}{f+d}, \text{ or}$$

$$\frac{\partial^2 W'}{\partial r^2} = 4\sqrt{3}\, c_2^0 \frac{f}{f+d}, \quad (8)$$

where the curvature of the vertex corrected wavefront can be calculated using Equation (6). Here, r represents the normalized pupil radius with values from 0 to 1, x and y are the normalized values in x- and y-axis, f is the local focal length, or the reciprocal of local power, and $c_2^0$ is the Zernike coefficient of defocus term. From the definition of power, we have $$\frac{\partial^2 W}{\partial r^2} = 4\sqrt{3}\, c_2^0 \quad (9)$$

$$S = \frac{1}{R^2} \frac{\partial^2 W}{\partial r^2}.$$

$$S' = \frac{1}{R^2} \frac{\partial^2 W'}{\partial r^2}$$

From Equations (8) and (9), we obtain the following formula $$S' = \frac{f}{f+d} S = \frac{S}{1+Sd}. \quad (10)$$

Equation (10) is the classical formula for vertex correction of pure sphere power, thus demonstrating that vertex correction can be effectively used in wavefront analysis.

(ii) Cylinder

In another example for astigmatism, $W(r, \theta)=c_2^{-2}\sqrt{6}r^2 \sin 2\theta + c_2^2\sqrt{6}r^2 \cos 2\theta$ corresponds to the wavefront at the second plane, a similar approach can be used to obtain the curvature of the corrected wavefront as $$\frac{\partial^2 W'}{\partial r^2} = (2\sqrt{6}\, c_2^{-2}\sin 2\theta + 2\sqrt{6}\, c_2^2\cos 2\theta)\frac{f}{f+d} \quad (11)$$

$$= \frac{\partial^2 W}{\partial r^2} \frac{f}{f+d}.$$

Denoting P' and P as the curvatures of W' (converted wavefront) and W (measured wavefront) respectively, $$P' = P\frac{f}{f+d} \quad (12)$$

$$= \frac{P}{1+Pd}.$$

By replacing P with S+C, it is possible to obtain the classical vertex correction for cylinder $$C' = \frac{S+C}{1+d(S+C)} - S'. \quad (13)$$

(iii) Coma

In addition to the low order wavefront vertex corrections discussed above, it is also possible to use vertex correction with wavefront measurements that include high order aberrations. For example, horizontal coma can be expressed as $W(r, \theta) = \sqrt{8} c_3^1 (3r^3 - 2r)\cos\theta$, again corresponding to the wavefront at the second plane. With an approach similar to that described above, it is possible to calculate the derivatives to x and to y and then calculate the curvature to r as $$\frac{\partial^2 W'}{\partial r^2} = \frac{f}{f+d} 18\sqrt{8}\, c_3^1 x \quad (14)$$
$$= \frac{\partial^2 W}{\partial r^2} \frac{f}{f+d}.$$

Denoting P' and P as the curvatures of W' (converted wavefront) and W (measured wavefront) respectively, $$P' = P\frac{f}{f+d} \quad (15)$$
$$= \frac{P}{1+Pd}.$$

(iv) Spherical Aberrations

In another example, a spherical aberration can be expressed as $W(r) = \sqrt{5} c_4^0 (6r^4 - 6r^2 + 1)$. Again, with an approach similar to that described above, it is possible to calculate the derivatives to x and to y and then calculate the curvature to r to determine the curvature of the corrected wavefront as $$\frac{\partial^2 W'}{\partial r^2} = \frac{f}{f+d}(72r^2 - 12)\sqrt{5}\, c_4^0 \quad (16)$$
$$= \frac{\partial^2 W}{\partial r^2} \frac{f}{f+d}.$$

Denoting P' and P as the curvatures of W' (converted wavefront) and W (measured wavefront) respectively, $$P' = P\frac{f}{f+d} \quad (17)$$
$$= \frac{P}{1+Pd}.$$

Therefore, for low order aberrations as well as for high order aberrations, it can be shown that by means of a slope scaling as applied in wavefront, it is possible to achieve the effect of power change as defined in a classical sense. Such approaches can be useful in determining treatment surface aberrations based on measurement surface aberrations.

2. New Algorithm for Vertex Correction

Treatment surface aberrations can also be determined based on various algorithmic approaches. In some embodiments, the treatment surface aberration is a treatment surface wavefront map. The treatment surface wavefront map can be derived at least in part by local slope scaling of a measurement surface wavefront map. For example, a treatment surface wavefront map can be derived at least in part by applying a scaling factor of 1/(1+Pd) to a slope of a measurement surface wavefront map, where P represents a local curvature of the measurement surface wavefront map and d represents a difference between a measurement surface and a treatment surface. For example, P can be based on a second derivative of the measurement surface wavefront map. P can also be based on a pupil radius of the eye. The following examples illustrate algorithmic approaches that incorporate such principles.

a. Constant HOA

This algorithm assumes that the average curvature for low order aberrations (LOA), as manifested by sphere and cylinder power terms, is affected by vertex distance change. High order aberrations (HOA) are considered as local irregularity add-ons to the mean curvature, and are not affected by vertex distance change. Thus, a total wavefront map can be separated into low order and high order portions as shown by the following formula $$W(x,y) = W_L(x,y) + W_H(x,y). \quad (18)$$

For the low order portion, it is possible to obtain the sphere and cylinder power terms by means of a Zernike decomposition method $$[S,C] = ZD[W_L(x,y)], \quad (19)$$

where S and C represent the sphere and cylinder power terms, respectively, and ZD represents a Zernike decomposition operator. The vertex corrected sphere S' and cylinder C' power terms can be obtained from the following formulae $$S' = \frac{S}{1+dS}, \quad (20)$$

$$C' = \frac{S+C}{1+d(S+C)} - S'. \quad (21)$$

The vertex corrected wavefront can then be obtained by adding the uncorrected high order portion of the original wavefront with the Zernike expansion operator applied to the corrected sphere S' and cylinder C' as $$W'(x,y) = ZE(S',C') + W_H(x,y), \quad (22)$$

where ZE stands for a Zernike expansion operator.

b. Varying HOA

This algorithm segments the wavefront measurement into multiple portions, and is designed to have each portion of the corrected wavefront focused on or toward the focal point of the optical system, regardless of the wavefront shape. Thus, the local slope of each portion of the wavefront measurement can be scaled by a factor of f/(f+d) where f represents the local focal length and d represents the vertex distance. By applying the following algorithms, it is possible to obtain the vertex corrected wavefront:

1. Calculate x- and y-gradient by the following algorithm:
   Along the x axis:
   a. $\partial W/\partial x = [W(i, j+1) - W(i, j)]/dx$ if [i,j] lands on left edge b. $\partial W/\partial x = [W(i, j) - W(i, j-1)]/dx$ if [i,j] lands on right edge
c. $\partial W/\partial x = [W(i, j+1) - W(i, j-1)]/2dx$ otherwise within pupil Along the y axis:
d. $\partial W/\partial y = [W(i, j) - W(i+1, j)]/dy$ if [i,j] lands on upper edge
e. $\partial W/\partial y = [W(i-1, j) - W(i, j)]/dy$ if [i,j] lands on lower edge
f. $\partial W/\partial y = [W(i-1, j) - W(i+1, j)]/2dy$ otherwise within pupil If [i,j] is outside the pupil, the data is not considered.

2. Calculate local curvature P using this algorithm:

a. Calculate $\frac{\partial^2 W}{\partial x^2}, \frac{\partial^2 W}{\partial y^2}$ and $\frac{\partial^2 W}{\partial x \partial y}$ from $\frac{\partial W}{\partial x}$ and $\frac{\partial W}{\partial y}$ using algorithm 1.

b. $\frac{\partial^2 W}{\partial r^2} = \frac{x^2}{x^2+y^2}\frac{\partial^2 W}{\partial x^2} + \frac{2xy}{x^2+y^2}\frac{\partial^2 W}{\partial x \partial y} + \frac{y^2}{x^2+y^2}\frac{\partial^2 W}{\partial y^2}$ c. Calculate local curvature $P = \frac{1}{R^2}\frac{\partial^2 W}{\partial r^2}$ (R being pupil radius)

3. Scale the wavefront local curvature with this algorithm:

$$\frac{\partial W'}{\partial x} = \frac{1}{1+Pd}\frac{\partial W}{\partial x}$$
$$\frac{\partial W'}{\partial y} = \frac{1}{1+Pd}\frac{\partial W}{\partial y}$$

4. Reconstruct the corrected wavefront W'(x,y) with this algorithm:
   a. Calculate Fourier transform of $\partial W'/\partial x$ and $\partial W'/\partial y$ to get $c_u$ and $c_v$, respectively.
   b. Multiply u with $c_u$ and v with $c_v$ and divide by $u^2+v^2$.
   c. Inverse Fourier transform to get W'(x,y).
   d. Calculate $\partial W'/\partial x$ and $\partial W'/\partial y$ using algorithm 1, adjusted with the edge being the entire frame as oppose to pupil edge.
   e. Replace $\partial W'/\partial x$ and $\partial W'/\partial y$ with values from step 3 within the pupil, leave values outside pupil untouched.
   f. Determine if a predefined criteria is met, or if a predetermined number of iterations have been completed. If not, go to step (a) and repeat through step (f).
   g. Provide an estimate of W'(x,y).

A predefined criteria of step (f) could be, for example, the RMS error of the reconstructed wavefront based on a comparison between $W'_i$ and $W'_{i-1}$, in the ith and (i-1)th iterations, respectively. Alternatively, other optical quality gauges may be used. In one embodiment, the predetermined number of iterations in step (f) is 10. As illustrated in the above algorithm, it is possible to derive a treatment surface wavefront map based on an iterative Fourier reconstruction algorithm. Thus the entire algorithm, steps 1 to 4, uses both Fourier reconstruction (step 4) and local slope scaling (step 3).

The theory behind Fourier reconstruction can be described as follows. Suppose wavefront W(x,y) is expanded into Fourier series as $$W(x,y) = \int\int c(u,v)\exp[i2\pi(ux+vy)]dudv,\quad (23)$$

where c(u, v) is the expansion coefficient. Taking partial derivative to x and y, respectively in the above equation, provides $$\begin{cases}\frac{\partial W(x,y)}{\partial x} = i2\pi\int\int uc(u,v)\exp[i2\pi(ux+vy)]dudv \\ \frac{\partial W(x,y)}{\partial y} = i2\pi\int\int vc(u,v)\exp[i2\pi(ux+vy)]dudv\end{cases}\quad (24)$$

Denoting $c_u$ to be the Fourier transform of x-derivative of W(x,y) and $c_v$ to be the Fourier transform of y-derivative of W(x,y), provides $$\begin{cases}\frac{\partial W(x,y)}{\partial x} = \int\int c_u(u,v)\exp[i2\pi(ux+vy)]dudv \\ \frac{\partial W(x,y)}{\partial y} = \int\int c_v(u,v)\exp[i2\pi(ux+vy)]dudv\end{cases}\quad (25)$$

Comparing these two sets of equations, provides $$\begin{cases}c_u(u,v) = i2\pi u c(u,v) \\ c_v(u,v) = i2\pi v c(u,v)\end{cases}\quad (26)$$

Combining these two equations with u multiplied in both sides of the first equation and v multiplied in both sides of the second equation, provides $$uc_u(u,v)+vc_v(u,v)=i2\pi(u^2+v^2)c(u,v).\quad (27)$$

Therefore, the Fourier transform of wavefront can be obtained as $$c(u,v) = -\frac{i[uc_u(u,v)+vc_v(u,v)]}{2\pi(u^2+v^2)} = \quad (28)$$
$$-\frac{i}{2\pi(u^2+v^2)}\left[u\int\int\frac{\partial W(x,y)}{\partial x}\exp[-i2\pi(ux+vy)] + v\int\int\frac{\partial W(x,y)}{\partial y}\exp[-i2\pi(ux+vy)]\right]$$

Hence, taking an inverse Fourier transform, it is possible to obtain the wavefront as $$W(x,y) = \int\int c(u,v)\exp[i2\pi(ux+vy)]dudv.\quad (29)$$

III. Refractive Treatment Shape

Once a treatment surface aberration has been derived by a method as described above, it is possible to determine a prescription or a refractive treatment shape based on the treatment surface aberration. For example, a prescription can be derived for ameliorating a vision condition in an eye of a patient. A refractive treatment shape can be determined based on the treatment surface aberration of the eye, and a refractive treatment shape can be embodied in any of a variety of corrective optical devices or procedures, including refractive laser surgery, spectacles, contact lenses, intraocular lenses, and the like.

IV. Example: Evaluating Classical Formulas and New Algorithms

Figure 7A:
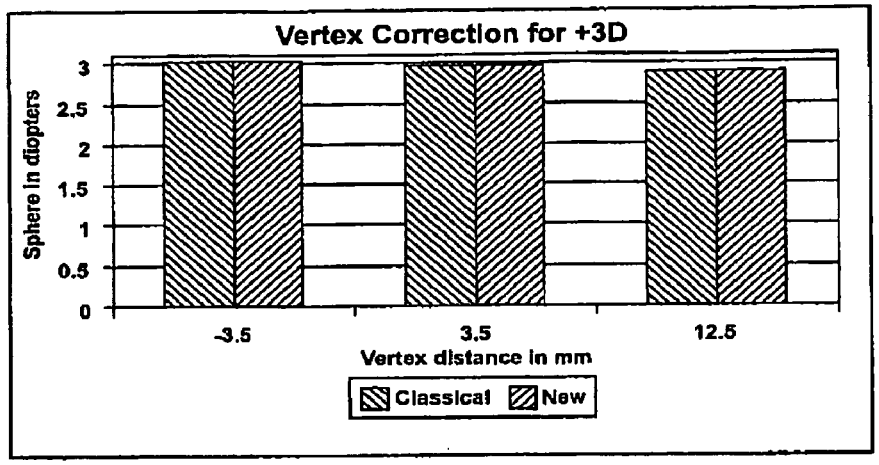
FIG. 7 illustrates a comparison between vertex corrected power calculations based on algorithms provided by the present invention with calculations based on a classical formula.
Figure 7B:
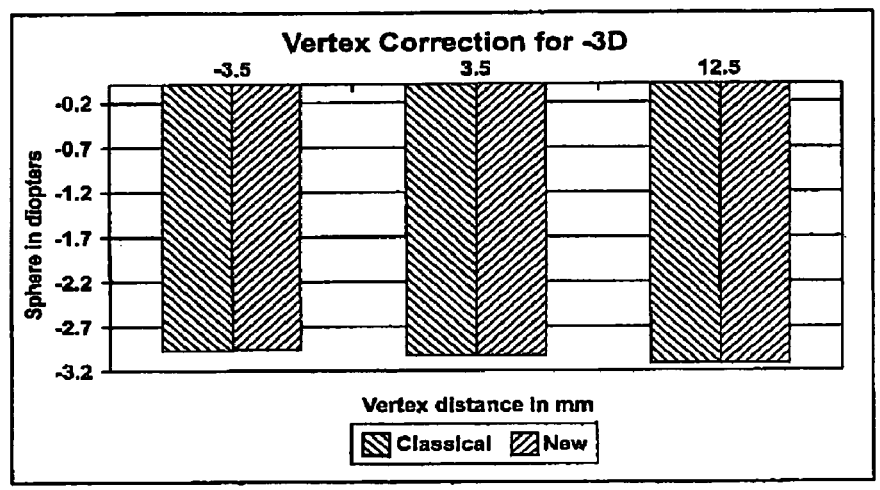
Figure 7C:
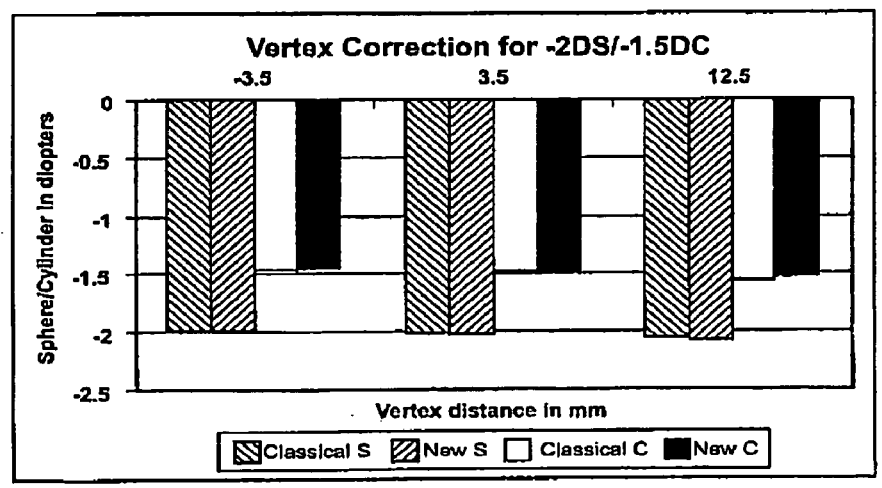

In some embodiments, it is useful to evaluate the convergence of Fourier reconstruction used in the vertex correction algorithms discussed above. Such approaches are discussed in commonly owned patent application Ser. No. 10/601,048 filed Jun. 20, 2003, the entirety of which is hereby incorporated by reference. It is also useful to evaluate the accuracy of the varying high order aberration algorithm as compared to the classical formulas discussed above (i.e. sphere, sphere and cylinder). For example, one test is to show the comparison between the algorithmic approaches and the traditional approaches for myopic, hyperopic, and astigmatism cases. FIG. 7 shows the comparison of vertex corrected sphere and cylinder using the varying high order aberration algorithm described above as compared to classical formulas (i.e. sphere, sphere and cylinder) for (a) hyperopia+3D; (b) myopia−3D; (c) astigmatism−2DS/−1.5DC. It is quite clear that the results are very good. Good results can be shown by a small error. For example, if the difference is less than 0.05D, or smaller than 2.5%, it can generally be considered good. For pure sphere cases (e.g. myopia and hyperopia), the error can be larger, due to coarse sampling of wavefront data in the calculation.

Figure 8:
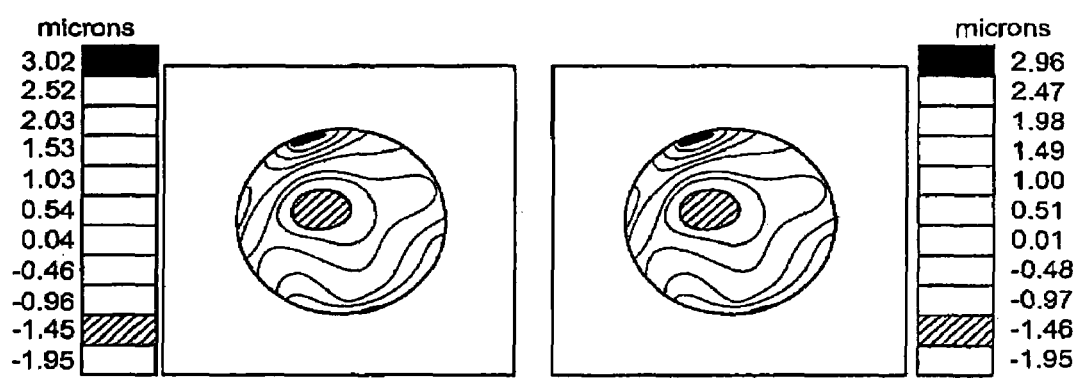
FIG. 8 illustrates a wavefront before and after a vertex correction.

For high order aberrations, it has been shown with two examples (i.e. coma, spherical aberrations) in theory that the vertex corrected wavefront follows the power relationship given by the classical formula of vertex correction. FIG. 8 shows wavefront surface plots of a pre-vertex correction (left panel) and post-vertex correction (right panel) corresponding to a 12.5 mm vertex correction as accomplished by a varying high order aberration algorithm.

In terms of the efficiency of a varying high order aberration algorithm, the following table shows the running time taken for such a vertex correction algorithm with respect to the number of iterations taken in the Fourier reconstruction, corresponding to step 4 of the algorithm, in a 1.13 GHz laptop computer. With 10 iterations, the algorithm can take more than 2 seconds in real time. Fortunately, this vertex correction may only be needed when a treatment table is generated, which in itself may take minutes. Treatment tables are files that can store commands for a laser to deliver individual laser pulses, in the context of a laser ablation treatment. For example, the commands can be for laser pulse duration and size.

| | Iterations | | | | | | |
|---|---|---|---|---|---|---|---|
| | 1 | 2 | 5 | 10 | 20 | 50 | 200 |
| Time (s) | 0.340 | 0.521 | 1.231 | 2.303 | 4.256 | 10.40 | 41.34 |

Thus in one embodiment, as part of the algorithm, Fourier reconstruction can require about 10 iterations to achieve planned results given by 100-micron sampling rate.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A method of determining a refractive treatment shape for ameliorating a vision condition in a patient, the method comprising:

a) measuring a wavefront aberration of an eye of the patient, the wavefront aberration corresponding to a measurement surface that is disposed at or near a pupil plane of the eye, in order to provide a measurement surface aberration comprising a measurement surface wavefront map;

b) deriving a treatment surface aberration of the eye, the treatment surface aberration corresponding to a treatment surface of the eye and comprising a treatment surface wavefront map derived at least in part by local slope scaling of the measurement surface wavefront map, the treatment surface aberration derived from the measurement surface aberration using a difference between the measurement surface and the treatment surface; and c) determining the refractive treatment shape based on the treatment surface aberration of the eye.

2. The method of claim 1, wherein the treatment surface is disposed at or near an anterior corneal surface of the eye.

3. The method of claim 1, wherein the treatment surface corresponds to a spectacle plane of the eye.

4. The method of claim 1, wherein the treatment surface is disposed posterior to a pupil plane of the eye.

5. The method of claim 1, wherein the treatment surface wavefront map is derived at least in part by applying a scaling factor of $1/(1+Pd)$ to a slope of the measurement surface wavefront map, where P represents a local curvature of the measurement surface wavefront map and d represents a difference between the measurement surface and the treatment surface.

6. The method of claim 5, wherein P is based on a second derivative of the measurement surface wavefront map.

7. The method of claim 6, wherein P is based on a pupil radius of the eye.

8. The method of claim 7, wherein the treatment surface wavefront map is derived according to an iterative Fourier reconstruction algorithm.

9. The method of claim 8, wherein the iterative Fourier reconstruction algorithm comprises 10 iterations.

10. The method of claim 1, wherein the measurement surface aberration reflects low order and high order aberrations of the eye of the patient.

11. The method of claim 1, wherein a difference between the measurement surface and a retinal surface of the eye corresponds to a first vertex measure, and a difference between the treatment surface and the retinal surface of the eye corresponds to a second vertex measure.

12. A method of ameliorating a vision condition in a patient, the method comprising:

a) measuring a wavefront aberration of an eye of the patient, the wavefront aberration corresponding to a measurement surface that is disposed at or near a pupil plane of the eye, in order to provide a measurement surface aberration, wherein the measurement surface aberration comprises low order and high order aberrations of the eye of the patient;

b) deriving a treatment surface aberration of the eye, the treatment surface aberration corresponding to a treatment surface of the eye, the treatment surface aberration derived from the measurement surface aberration using a difference between the measurement surface and the treatment surface;

c) determining a refractive treatment shape based on the treatment surface aberration of the eye; and d) applying the refractive treatment shape to the eye of the patient to ameliorate the vision condition.

13. The method of claim 12, wherein the treatment surface is disposed at or near an anterior corneal surface of the eye, and the refractive treatment shape is applied to the eye of the patient in a treatment modality selected from the group consisting of:
- (i) ablating a corneal surface of the eye to provide a corneal surface shape that corresponds to the refractive treatment shape, and
- (ii) providing the patient with a contact lens that has a shape that corresponds to the refractive treatment shape.

14. The method of claim 12, wherein the treatment surface corresponds to a spectacle plane of the eye, and the refractive treatment shape is applied to the eye of the patient by providing the patient with a spectacle lens that has a shape that corresponds to the refractive treatment shape.

15. The method of claim 12, wherein the treatment surface is disposed posterior to a pupil plane of the eye, and the refractive treatment shape is applied to the eye of the patient by providing the patient with an intra-ocular lens that has a shape that corresponds to the refractive treatment shape.

16. A system for generating a refractive treatment shape for ameliorating a vision condition in an eye of a patient, the system comprising:

- a) an input module that accepts a measurement surface aberration, the measurement surface aberration based on a wavefront aberration the eye, the wavefront aberration corresponding to a measurement surface that is disposed at or near a pupil plane of the eye, wherein a difference between the measurement surface and a retinal surface of the eye corresponds to a first vertex measure;
- b) a transformation module that derives a treatment surface aberration, the treatment surface aberration corresponding to a treatment surface of the eye, the treatment surface aberration derived from the measurement surface aberration using a difference between the measurement surface and the treatment surface, wherein a difference between the treatment surface and the retinal surface of the eye corresponds to a second vertex measure; and
- c) an output module that generates the refractive treatment shape based on the treatment surface aberration.

17. The system of claim 16, wherein the treatment surface is disposed at or near an anterior corneal surface of the eye.

* * * * *